United States Patent
Tseng et al.

(10) Patent No.: US 9,733,250 B2
(45) Date of Patent: Aug. 15, 2017

(54) DEVICE FOR CAPTURING CIRCULATING CELLS

(71) Applicant: The Regents of the University of California, Oakland, CA (US)

(72) Inventors: Hsian-Rong Tseng, Los Angeles, CA (US); Shutao Wang, Los Angeles, CA (US); Hao Wang, Los Angeles, CA (US); Kan Liu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/834,024

(22) Filed: Aug. 24, 2015

(65) Prior Publication Data

US 2016/0209418 A1 Jul. 21, 2016

Related U.S. Application Data

(63) Continuation of application No. 13/256,879, filed as application No. PCT/US2010/027816 on Mar. 18, 2010, now Pat. No. 9,140,697.

(60) Provisional application No. 61/161,248, filed on Mar. 18, 2009, provisional application No. 61/301,839, filed on Feb. 5, 2010.

(51) Int. Cl.
 *G01N 33/543* (2006.01)
 *G01N 33/574* (2006.01)
 *B01L 3/00* (2006.01)

(52) U.S. Cl.
 CPC .. *G01N 33/57492* (2013.01); *B01L 3/502707* (2013.01); *B01L 3/502761* (2013.01); *G01N 33/54366* (2013.01); *B01L 2200/0668* (2013.01); *B01L 2300/0636* (2013.01); *B01L 2300/0816* (2013.01); *B01L 2300/0877* (2013.01); *B01L 2300/0887* (2013.01)

(58) Field of Classification Search
 None
 See application file for complete search history.

(56) References Cited

U.S. PATENT DOCUMENTS

| 5,957,579 A | 9/1999 | Kopf-Sill et al. |
| 2004/0262223 A1 | 12/2004 | Strook et al. |
| 2007/0238186 A1 | 10/2007 | Sun et al. |
| 2010/0285972 A1 | 11/2010 | Dubrow et al. |

FOREIGN PATENT DOCUMENTS

| CN | 1871517 A | 11/2006 |
| WO | WO-2007/106598 A2 | 9/2007 |

OTHER PUBLICATIONS

Adams et al., "Highly Efficient Circulating Tumor Cell Isolation from Whole Blood and label-Free Enumeration Using Polymer-Based Microfluidics with an Integrated Conductivity Sensor". *J Am Chem Soc* 130, 8633-8641 (2008).

Allard et al., "Tumor Cells Circulate in the Peripheral Blood of All Major Carcinomas but not in Healthy Subjects or Patients With Nonmalignant Diseases". *Clinical Cancer Research* 10, 6897-6904 (2004).

(Continued)

*Primary Examiner* — Chris L Chin
(74) *Attorney, Agent, or Firm* — Venable LLP; Henry J. Daley

(57) ABSTRACT

The present invention provides devices and methods for capturing rare cells. The devices and methods described herein can be used to facilitate the diagnosis and monitoring of metastatic cancers.

13 Claims, 10 Drawing Sheets

(56) References Cited

OTHER PUBLICATIONS

Budd et al., "Circulating Tumor Cells versus Imaging—Predicting Overall Survival in Metastatic Breast Cancer". *Clinical Cancer Research* 12, 6403-6409 (2006).

Chang et al., Biomimetic technique for adhesion-based collection and separation of cells in a microfluidic channel. *Lab Chip* 5, 64-73 (2005).

Cristofanilli et al., "Circulating Tumor Cells, Disease Progression, and Survival in Metastatic Breast Cancer". *The New England Journal of Medicine* 351, 781-791 (2004).

Domagala et al., "Configuration of surfaces of human cancer cells in effusions". *Virchows Archie B Cell Pathology Zell-pathologie* 26, 27-42 (1978).

European Search Report issued in counterpart European Application No. 10754108.8 dated Aug. 13, 2012.

Fischer et al., "Biomimetic Nanowire Coatings for Next Generation Adhesive Drug Delivery Systems," Nano Letters, 2009 vol. 9, No. 2, pp. 716-720.

Huang et al., "Continuous Particle Separation Through Deterministic Lateral Displacement". *Science* 304, 987-990 (2004).

Krivacic et al., "A rare-cell detector for cancer". *Proceedings of the National Academy of Sciences of the United States of America* 101, 10501-10504 (2004).

Kwon et al., "Separation of Human Breast Cancer and Epithelial Cells by Adhesion Difference in a Microfluidic Channel," J. Semiconductor Tech & Sci, vol. 7, No. 3, 2007, 140-150.

Nagrath et al., "Isolation of rare circulating tumour cells in cancer patients by microchip technology". *Nature* 450, 1235-1239 (2007).

Racila et al., "Detection and characterization of carcinoma cells in the blood". *Proceedings of the National Academy of Sciences of the United States of America* 95, 4589-4594 (1998).

Sha et al., "Surface-Enhanced Raman Scattering Tags or Rapid and Homogeneous Detection of Circulating Tumor Cells in the Presence of Human Whole Blood," J Am Chem Soc 2008, 130(51), 17214-17215.

Smirnov et al., "Global Gene Expression Profiling of Circulating Tumor Cells". *Cancer Research* 65, 4993-4997 (2005).

Steeg, "Tumor metastasis: mechanistic insights and clinical challenges". *Nat Med* 12, 895-904 (2006).

Sun Duke et al., "Preparation, Characterization and Applications of One-Dimensional Nanostructures," Chinese Journal of Rare Materials, vol. 30, No. 1, 2006 (English Abstract).

Toner et al., "D. Blood-on-a-CIl1P". *Annual Review of Biomedical Engineering* 7, 77-103 (2005).

Wang et al., "Three-Dimensional Nanostructured Substrates toward Efficient Capture of Circulating Tumor Cells," Angew. Chem. Int. Ed. 2009, vol. 48, pp. 8970-8973.

Zieglschmid et al., "0. Detection of Disseminated Tumor Cells in Peripheral Blood". *Critical Reviews in Clinical Laboratory Sciences* 42, 155-196 (2005).

Figure 2A
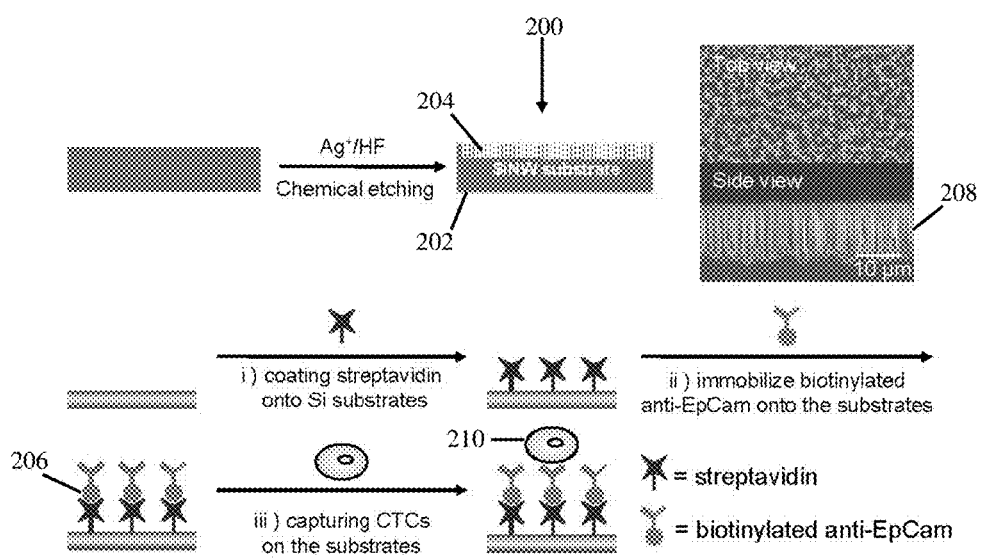
Figure 2B
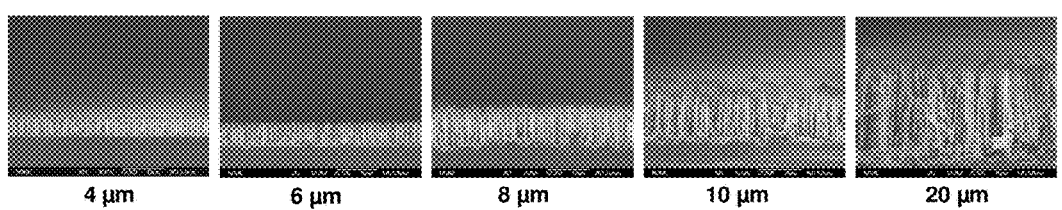
Figure 2C

Figure 3A
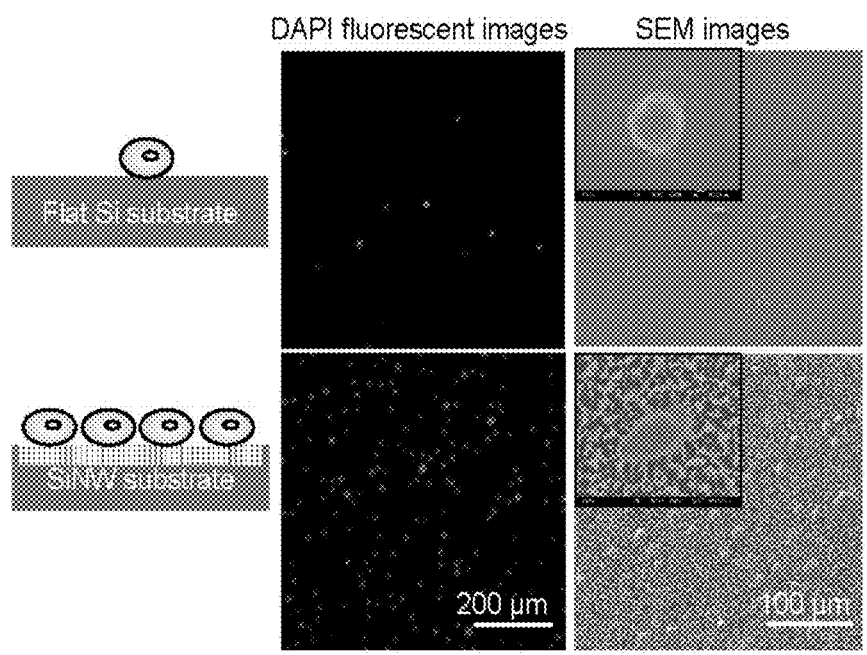
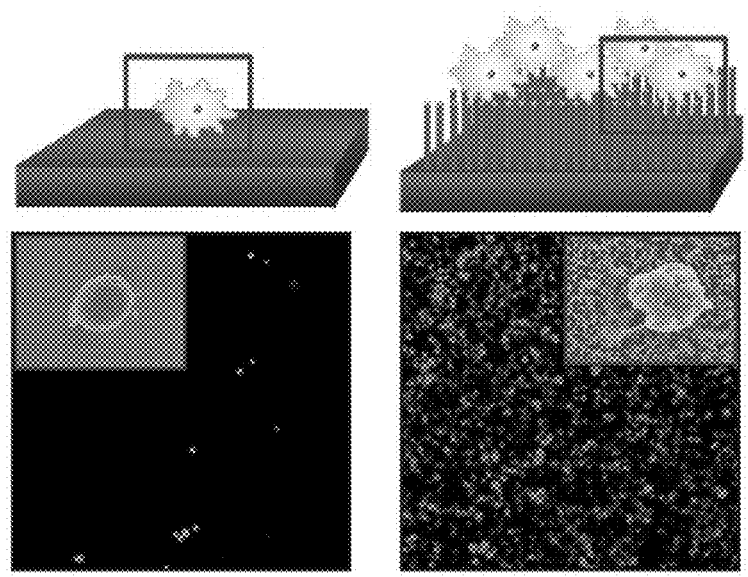
Figure 3B

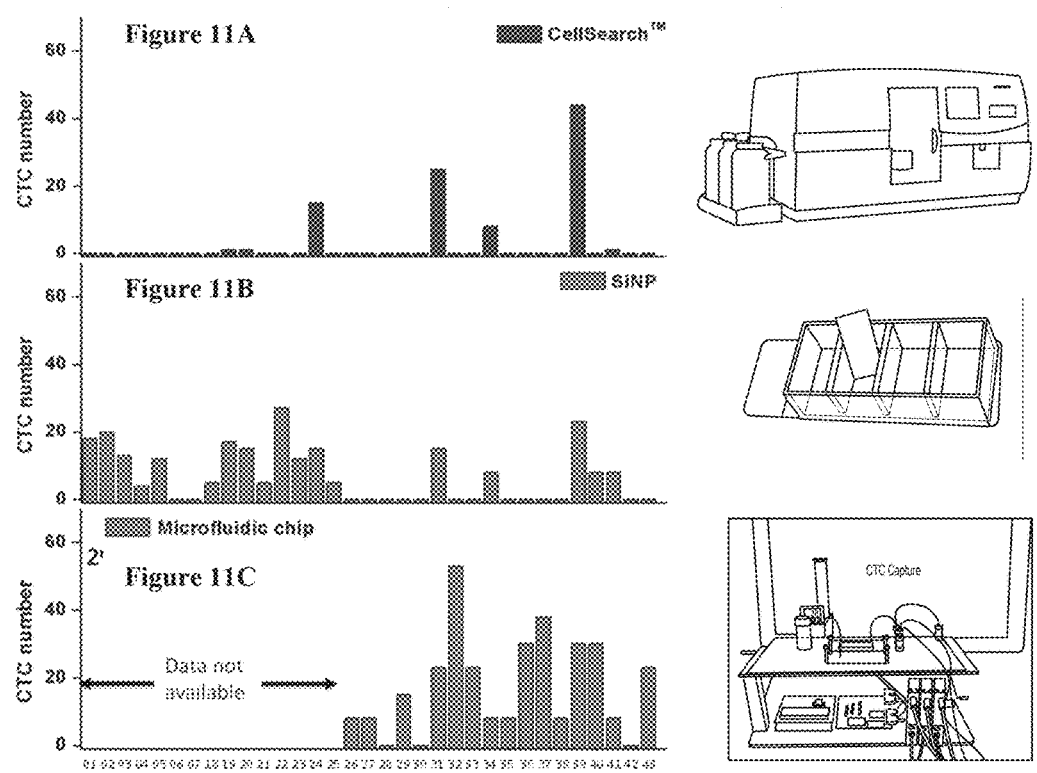

DEVICE FOR CAPTURING CIRCULATING CELLS

This application is a continuation of U.S. application Ser. No. 13/256,879 filed Sep. 15, 2011, which is a National Stage of International Application No. PCT/US2010/027816 filed Mar. 18, 2010, and claims priority to U.S. provisional application No. 61/161,248, filed on Mar. 18, 2009, and 61/301,839, filed on Feb. 5, 2010, the entire contents of which are incorporated herein by reference.

This invention was made with Government support under CA119347 awarded by the National Institutes of Health. The Government has certain rights in the invention.

BACKGROUND

1. Field of Invention

The present invention relates to devices and methods for capturing rare cells.

2. Background Information

Cancer is one of the leading causes of death in the developed world, resulting in over 500,000 deaths per year in the United States alone. Over one million people are diagnosed with cancer in the U.S. each year, and overall it is estimated that more than 1 in 3 people will develop some form of cancer during their lifetime.

Most cancer patients are not killed by their primary tumor. Instead, cancer patients succumb to metastases: the spread of malignant cells from one part of the body to another. If a primary tumor is detected early enough, it can often be eliminated by surgery, radiation, chemotherapy or some combination of these treatments. In contrast, metastatic tumors are difficult to detect and treatment becomes more challenging as metastases progresses. As such, there is a need to develop methods for detecting early-stage cancer metastasis.

Cancer cells that break away from the primary tumor site are known as circulating tumor cells (CTCs).[1] CTCs represent a potential alternative to invasive biopsies as a source of tumor tissue for the detection, characterization, and monitoring of non-hematologic cancers.[2-4] Over the past decade, CTCs have become an emerging "biomarker" for detecting early-stage cancer metastasis, predicting patient prognosis, as well as monitoring disease progression and therapeutic outcomes of cancer.[5] However, isolation of CTCs have been technically challenging due to the extremely low abundance (a few to hundreds per mL) of CTCs among a high number of hematologic cells ($10^9$ cells/mL) in the blood.[4,6,7]

Previous approaches for enriching or sorting CTCs from peripheral blood include flow cytometry, immunomagnetic beads, high-throughput optical-imaging systems, and fibre optic array scanning. Immunomagnetic-bead purification of CTCs is currently the most widely used technology in the clinical setting, and has successfully identified CTCs in patients with lung, prostate, colon, breast, and pancreatic cancer.[3,4,8-10] However, this approach isolates small numbers of CTCs (4±24 (mean±s.d.) per ml in lung; 11±118 in breast; 10±33 in prostate; and 1±2 in both colorectal and pancreatic cancers)[3] with very low purity (0.01-0.1%)[10], and low yield (~20-60% of patients)[3]. The level of "biological noise" associated with the low sensitivity, selectivity, and yield of immunomagnetic-bead technologies restricts their use in early cancer detection and in monitoring patient response to treatment. At present, immunomagnetic-bead technology is useful as a gross prognostic tool, classifying patients into high- and low-risk categories.[5]

Microfluidic lab-on-a-chip devices provide unique opportunities for cell sorting and rare-cell detection. Microfluidic technology has been successfully used for microfluidic flow cytometry, continuous size-based separation[11] and chromatographic separation[12]; however, these methods are unable to process large sample volumes (e.g., milliliters of whole blood)[13]. Microfluidic technology has also been used to capture CTCs from whole blood samples.[8,9] However, existing CTC-capture systems require complicated fluidic handling systems to introduce blood flow through the devices. Furthermore, these systems use microstructures, which are not optimal for cell capture, to isolate CTCs.

The surfaces of most tumor cells of epithelial origin (carcinomas) are covered with nanoscaled microvilli of variable sizes and configuration.[14] In benign epithelial cells of glandular origin, the microvilli are polarized (i.e., confined to one aspect of the normal cell, usually that facing the lumen of a gland or organ) and are of uniform and monotonous configuration. The microvilli of epithelial cancer cells cover the entire cell surface, vary in size and length, and sometimes form clumps of very long microvilli. In some tumors, notably carcinomatous mesothelioma, tufts of long microvilli characterize the malignant cells. Furthermore, additional structures are present on the cell surface, which are also nanoscale in size, including lamellipodia, filopodia, and lipid-raft molecular groups. Some embodiments of the present invention proposes a new generation of cell capture devices that takes advantage of the presence of these nanoscaled structures on the cell surface.

SUMMARY

Further objectives and advantages will become apparent from a consideration of the description, drawings, and examples.

A device for capturing cells according to embodiments of the present invention has a substrate containing a nanostructured surface region. Attached to the nanostructured surface region is a plurality of binding agents, which are capable of selectively capturing target cells in a cell sample. The nanostructured surface region contains a plurality of nanostructures. The nanostructures have a longitudinal dimension and a lateral dimension, and in some embodiments, the longitudinal dimension is at least ten times greater than the lateral dimension.

In some embodiments or the present invention, the device is a microfluidic device. The microfluidic device has a substrate attached to a flow layer, forming a microfluidic channel. The substrate has a nanostructured surface region, a portion of which is in contact with fluid that flows through the microfluidic channel while in operation. The nanostructured surface region contains a plurality of nanostructures each having a longitudinal dimension and a lateral dimension. Attached to the nanostructured surface region is a plurality of binding agents, which are capable of selectively capturing target cells in a cell sample.

Embodiments of the present invention are also directed to a method of isolating target cells from a cell sample. The method involves providing a cell sample having at least one target cell and contacting the cell sample with a plurality of nanostructures. Attached to the nanostructures is a plurality of binding agents, which is capable of selectively capturing the target cells in the cell sample.

Other embodiments of the present invention are directed to using the methods and devices of the present invention to diagnose disease, monitor disease progression, and evaluate the efficacy of a treatment.

Further embodiments of the present invention are directed to kits that contain a device of the present invention.

BRIEF DESCRIPTION OF THE DRAWINGS

FIGS. 2A-2C illustrate the preparation of silicon nanowires (SiNWs) according to an embodiment of the present invention. FIG. 2A shows chemical etching by $Ag^+$ and HF to introduce a SiNW array onto a silicon wafer. The scanning electron microscope (SEM) images reveal well-defined SiNWs with diameters ranging from 100 to 200 nm and length around 10 µm. FIG. 2B is a schematic presentation of grafting biotinylated epithelial cellular adhesion molecule antibodies (anti-EpCam) onto silicon substrates. FIG. 2C shows SEM images of SiNW substrates with different SiNW lengths obtained by wet chemical etching.

FIGS. 3A-3C compare flat silicon substrates and SiNW substrates, which are embodiments of the present invention. FIG. 3A shows fluorescence microscope images and SEM images of SiNW substrates and flat silicon substrates, on which MCF7 were captured. FIG. 3B shows fluorescence microscope images and SEM images of SiNW substrates and flat silicon substrates, on which Daubi B cells were captured. In FIGS. 3A and 3B, the SiNW substrates exhibited significantly higher cell capture efficiency than the flat ones. FIG. 3C is a schematic depiction of the photolithography process for patterning alternating SiNW and flat substrates on a silicon wafer for comparing cell capture efficiency in a close experimental setting.

FIG. 4A shows the correlation between cell capture efficiency and capture times. FIG. 4B shows the correlation between cell capture efficiency and different SiNW lengths ranging from 0 to 20 µm.

FIG. 6A is a photograph of the microfluidic cell capture platform. FIG. 6B is a schematic representation of the integrated CTC capture platform composed of a capture agent-coated SiNW substrate and an overlaid microfluidic chaotic mixer. FIG. 6C is an optical image of the SiNW pattern underneath chaotic mixing channels. FIG. 6D is a side-view SEM image of the well-defined SiNWs with diameters ranging from 100 to 200 nm and lengths around 10 µm. FIG. 6E shows how cell surface components attach onto the nanostructured substrate with high efficiency, presumably because nanostructured substrates enhance the local interaction with cell surface components.

FIG. 7A shows the correlation between flow rate and capture yield in the microfluidic device. FIG. 7B shows the distribution of capture cells in the microchannel from inlet to outlet (0 to 88 cm). FIG. 7C is a photograph of the microfluidic device.

FIG. 10A shows the correlation between cell capture efficiency and capture times. FIG. 10B shows the correlation between cell capture efficiency and different SiNW lengths ranging from 0 to 20 µm. FIG. 10C shows the percentage of targeted Daudi B cells that are captured in a cell mixture at different ratios. FIG. 10D is a fluorescent image of Daudi B cells captured on the SiNP substrates. Each plot and error bar represents a mean±standard deviation from three repeats.

FIGS. 11A-11C compare the capture capabilities of devices according to embodiments of the present invention and Cellsearch™ technology. FIG. 11A shows the CTC numbers reported for 43 metastatic prostate cancer patient samples. FIG. 11B shows the CTC numbers reported for the patient samples using a device according to an embodiment of the present invention under static incubation conditions. FIG. 11C shows the CTC numbers reported for the patient samples using a microfluidic device according to an embodiment of the present invention.

DETAILED DESCRIPTION

Figure 1:
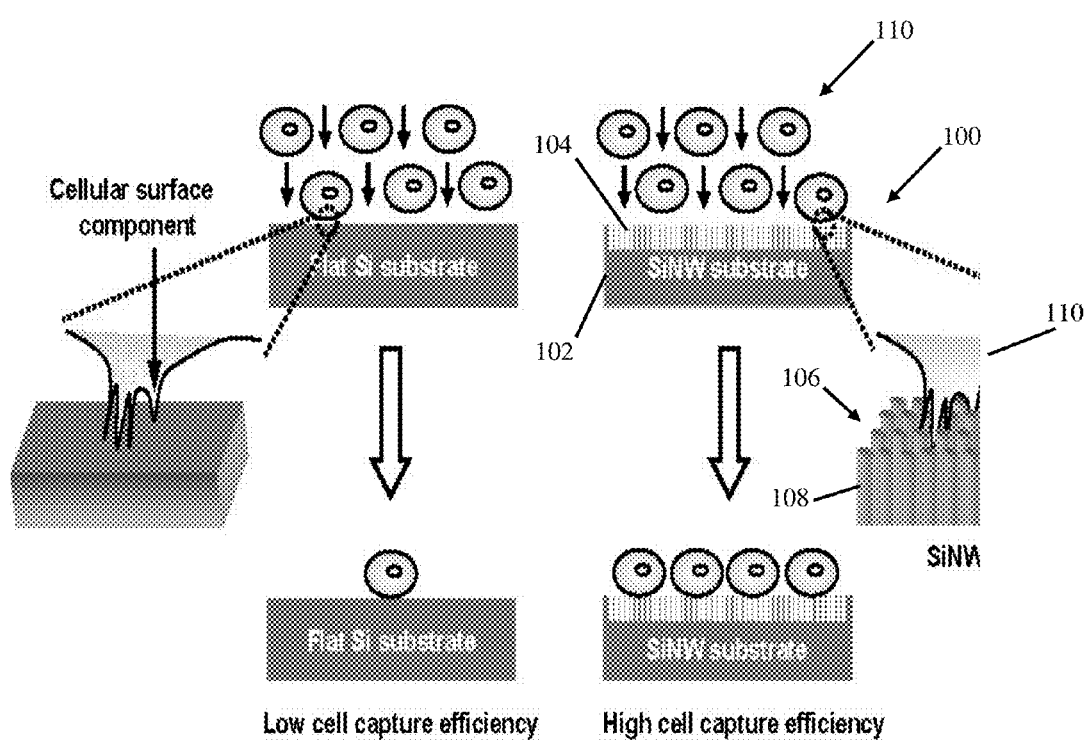
FIG. 1 provides a conceptual illustration of how a nanostructured substrate can be employed to achieve improved cell-capture efficiency from a sample according to an embodiment of the present invention. More cell surface components attach onto nanostructured substrates than flat substrates because nanostructured substrates provide enhanced local interaction with cell surface components.

Some embodiments of the present invention are directed to a device that is capable of rapidly and efficiently separating rare cells, e.g., CTCs, from biological samples. The device contains a binding agent attached to a nanostructure. Cell capture is mediated by the interaction of the target cell with the binding agent. In addition, the nanostructure assists in cell capture by interacting with cellular surface components such as microvilli, lamellipodia, filopodia, and lipid-raft molecular groups. In addition to accurately identifying and measuring rare cells in biological samples, devices according to some embodiments of the present invention isolate rare cells that can be used in subsequent processes. Some embodiments of the present invention are further directed to using the device in both research and clinical management, including using the device to detect, diagnosis, and monitor disease.

In some embodiments, the devices and methods of the present invention are able to sort rare cells directly from whole blood in a single step. For example, devices and methods according to embodiments of the present invention are capable of utilizing whole, anticoagulated blood (although not limited thereto) without any further sample treatment steps, such as dilution, centrifugation, red blood cell lysis, cell fixation, or cell labeling. This contrasts with immunomagnetic-bead-based systems, which require multiple "bulk" semi-automated preparatory steps (centrifugation, washing, and incubation), resulting in loss and/or destruction of a significant portion of the rare cells. In addition, devices and methods according to embodiments of the present invention are capable of isolating both viable and fixed cells, whereas magnetic bead-based approaches can only isolate fixed, nonviable cells. Furthermore, unlike existing microfluidic CTC-capture devices that require complicated fluidic handling systems, devices according to embodiments of the present invention can achieve high cell-capture efficiency by statically incubating blood samples in the device.

Some embodiments of the devices and methods of the present invention are also distinctive in that they use nanostructures to capture and isolate circulating cells in a biological sample. Previous microfluidic CTC-capture devices employed microstructures to interact with target cells. These microstructures are capable of interacting with most cells, which are usually 10-30 µm in size. However, these microstructures cannot interact with the various components on the cellular surface that are nanoscale in size (e.g., microvilli). The nanostructures according to embodiments of the present invention enhance binding to the target cell by interacting with these nanoscopic cellular surface components.

In some embodiments, the devices and methods of the present invention can achieve capture of rare cells at high sensitivity (e.g., percentage of patients having a tumor identified as having CTCs); high specificity (e.g., percentage of patients not having a tumor identified as not having CTCs); and high purity (defined as the percentage of the rare cells retained by the device relative to other cells retained by the device). The observed levels of sensitivity, specificity, and purity are surprising in comparison to previous devices and methods for capturing CTCs. (See, e.g., FIG. 10).

In some embodiments, the devices and methods of the present invention are readily adaptable for potential use in various clinical scenarios, including changes in throughput and in the binding agent, allowing capture of any type of rare circulating cell. In addition, the devices and methods according to some embodiments of the present invention are not limited to identifying and isolating circulating tumor cells. The devices and methods according to embodiments of the present invention are suitable for use within a range of cytological research areas. The one-step potential and versatility of some embodiments of the present invention makes these embodiments conducive to point-of-care use and rapid integration into clinical practice.

Embodiments of the present invention are discussed in detail below. In describing embodiments, specific terminology is employed for the sake of clarity. However, these embodiments are not intended to be limited to the specific terminology so selected. One of ordinary skill in the relevant art will recognize that other equivalent components can be employed and other methods developed without departing from the spirit and scope of the invention. All references cited herein are incorporated by reference as if each had been individually incorporated.

1. DEFINITIONS

To facilitate an understanding of the present invention, a number of terms and phrases are defined below.

As used herein, the singular forms "a", "an", and "the" include plural forms unless the context clearly dictates otherwise. Thus, for example, reference to "a binding agent" includes reference to more than one binding agent.

The term "nanostructure" refers to a structure having a lateral dimension and a longitudinal dimension, wherein the lateral dimension, the longitudinal dimension, or both the lateral and longitudinal dimensions are less than 1 mm. The shape of the nanostructure is not critical. It can, for example, be any three dimensional surface such as a bead, particle, strand, tube, sphere, etc.

The terms "diagnostic" and "diagnosis" refer to identifying the presence or nature of a pathologic condition and includes identifying patients who are at risk of developing a specific disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "detection", "detecting" and the like, may be used in the context of detecting biomarkers, or of detecting a disease or disorder (e.g., when positive assay results are obtained). In the latter context, "detecting" and "diagnosing" are considered synonymous.

The terms "subject", "patient" or "individual" generally refer to a human, although the methods of the invention are not limited to humans, and should be useful in other mammals (e.g., cats, dogs, etc.).

"Sample" is used herein in its broadest sense. A sample may comprise a bodily fluid including blood, serum, plasma, tears, aqueous and vitreous humor, spinal fluid, urine, and saliva; a soluble fraction of a cell or tissue preparation, or media in which cells were grown. Means of obtaining suitable biological samples are known to those of skill in the art.

The term "binding agent" as used herein refers to any entity or substance, e.g., molecule, which is associated with (e.g., immobilized on, or attached either covalently or non-covalently to) the nanostructured surface region, or which is a portion of such surface (e.g., derivatized portion of a plastic surface), and which can undergo specific interaction or association with the target cell. A "plurality of binding agents" can refer to a plurality of one particular binding agent or a plurality of more than one binding agent.

An "antibody" is an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies generated from at least two intact antibodies, hybrid antibodies, fusion proteins comprising an antibody portion, and any other modified immunoglobulin molecule comprising an antigen recognition site so long as the antibodies exhibit the desired biological activity. An antibody may be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies may be naked or conjugated to other molecules such as toxins, radioisotopes, etc.

The term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

"Hybrid antibodies" are immunoglobulin molecules in which pairs of heavy and light chains from antibodies with different antigenic determinant regions are assembled together so that two different epitopes or two different antigens may be recognized and bound by the resulting tetramer.

"Isolated" in regard to cells, refers to a cell that is removed from its natural environment (such as in a solid tumor) and that is isolated or separated, and is at least about 30%, 50%, 75%, and 90% free from other cells with which it is naturally present, but which lack the marker based on which the cells were isolated.

That a molecule (e.g., binding agent) "specifically binds" to or shows "specific binding" or "captures" or "selectively captures" a target cell means that the molecule reacts or associates more frequently, more rapidly, with greater duration, and/or with greater affinity with the target cell than with alternative substances. Thus, under designated experimental conditions, the specified molecule bind to the target cell at least two times the background and does not substantially bind in a significant amount to other cells and proteins present in the sample.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

2. DEVICE

A device according to an embodiment of the present invention is illustrated schematically in FIGS. 1, 2A, and 2B. The device (100 and 200) contains a substrate (102 and 202) having a nanostructured surface region (104 and 204). A plurality of binding agents (106 and 206) is attached to said nanostructured surface region of said substrate. The nanostructured surface region comprises a plurality of nanostructures (such as nanostructure 108 and nanostructure 208) each having a longitudinal dimension and a lateral dimension. As a sample is placed on the device, biological cells (110 and 210) are selectively captured by the binding agents and the plurality of nanostructures acting in cooperation.

The binding agent or agents employed will depend on the type of biological cell(s) being targeted. Conventional binding agents are suitable for use in some of the embodiments of the present invention. Nonlimiting examples of binding agents include antibodies, nucleic acids, oligo- or polypeptides, cellular receptors, ligands, aptamers, biotin, avidin, coordination complexes, synthetic polymers, and carbohydrates. In some embodiments of the present invention, binding agents are attached to the nanostructured surface region using conventional methods. The method employed will depend on the binding agents and the material used to construct the device. Nonlimiting examples of attachment methods include non-specific adsorption to the surface, either of the binding agents or a compound to which the agent is attached or chemical binding, e.g., through self assembled monolayers or silane chemistry. In some embodiments, the nanostructured surface region is coated with streptavidin and the binding agents are biotinylated, which facilitates attachment to the nanostructured surface region via interactions with the streptavidin molecules.

In some embodiments of the present invention, the nanostructures increase the surface area of the substrate and increase the probability that a given cell will come into contact with a binding agent. In these embodiments, the nanostructures can enhance binding of the target cells by interacting with cellular surface components such as microvilli, lamellipodia, filopodia, and lipid-raft molecular groups. In some embodiments, the nanostructures have a longitudinal dimension that is equal to its lateral dimension, wherein both the lateral dimension and the longitudinal dimension is less than 1 µm, i.e., nanoscale in size. In other embodiments, the nanostructures have a longitudinal dimension that is at least ten times greater than its lateral dimension. In further embodiments, the nanostructures have a longitudinal dimension that is at least twenty times greater, fifty times greater, or 100 times greater than its lateral dimension. In some embodiments, the lateral dimension is less than 1 µm. In other embodiments, the lateral dimension is between 1-500 nm. In further embodiments, the lateral dimension is between 30-400 nm. In still further embodiments, the lateral dimension is between 50-250 nm. In some embodiments, the longitudinal dimension is at least 1 µm long. In other embodiments, the longitudinal dimension is between 1-50 µm long. In other embodiments, the longitudinal dimension is 1-25 µm long. In further embodiments, the longitudinal dimension is 5-10 µm long. In still further embodiments, the longitudinal dimension is at least 6 µm long.

The shape of the nanostructure is not critical. In some embodiments of the present invention, the nanostructure is a sphere or a bead. In other embodiments, the nanostructure is a strand, a wire, or a tube. In further embodiments, a plurality of nanostructure contains one or more of nanowires, nanofibers, nanotubes, nano-pillars, nanospheres, or nanoparticles.

The exact device geometry will be determined based on the assay. Devices may, or may not, include regions that allow for optical or visual inspection of the nanostructure surface.

In embodiments, high cell-capture efficiency can be achieved by statically incubating blood samples.

Figures 6A, 6B, 6C, 6D, 6E:
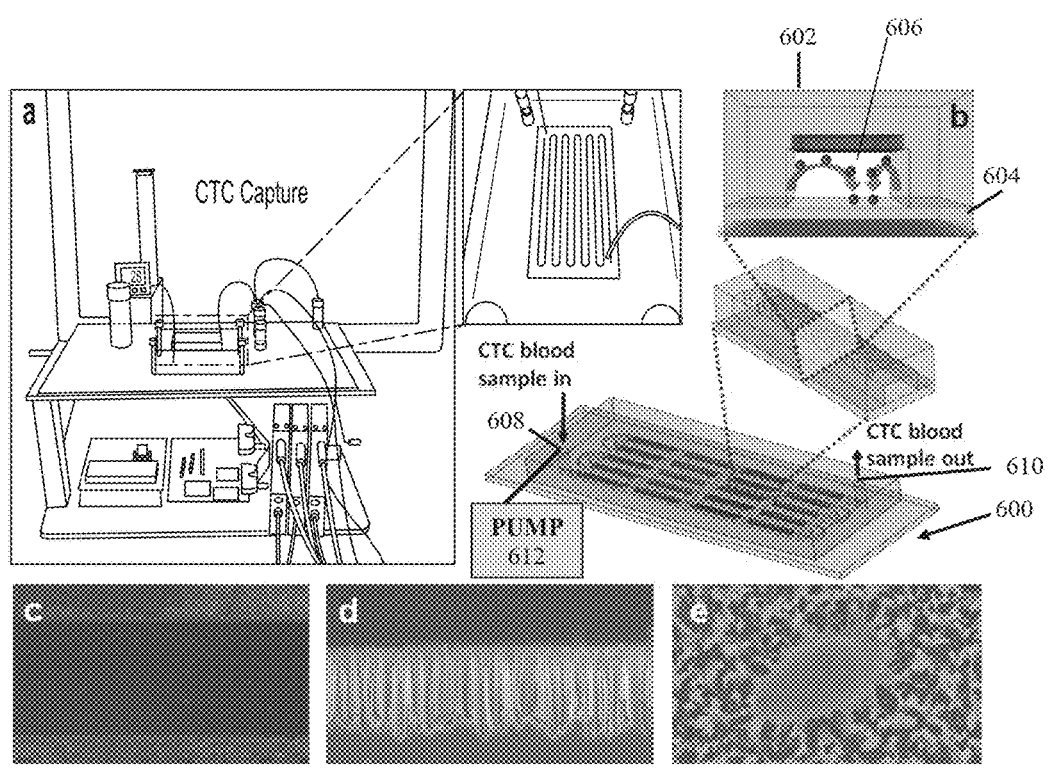
FIGS. 6A-6E depict a microfluidic device according to an embodiment of the present invention.

An embodiment of a microfluidic device (600) according to the present invention is illustrated schematically in FIG. 6B. The microfluidic device (600) has a flow layer (602) attached to the substrate (604) to form a microfluidic channel (606). In such a device (600), a portion of the nanostructured surface region of the substrate (604) will be in contact with fluid that flows through the microfluidic channel. The microfluidic device includes at least one fluid input microchannel (608). However, the microfluidic device is not limited to only one input microchannel. In some embodiments, the microfluidic device can include two or more input channels as well as two or more fluid sources that are in fluid connection. The microfluidic device also has one or more output microchannels (610) for egress of the fluid.

Nonlimiting examples of fluids that may be introduced into a device include washing buffers, e.g., to remove nonspecifically bound cells or unused reagents, lysing reagents, or labeling reagents, e.g., extracellular or intracellular stains. In some embodiments, devices of the present invention are designed to have removable covers to allow access to all or a region in which cells may be bound. With these devices, it is possible to apply reagents, e.g., labeling reagents or lysing reagents, to specific regions. Individual cells may also be removed from such. In other embodiments, the device has more than one input microchannel and output microchannel to allow the introduction of more than one fluid to the device, typically at different times. By having multiple input microchannels and corresponding output microchannels, fluids may be introduced simultaneously in the device to manipulate bound cells in specified regions. The size of these regions may be controlled based on the location of the input microchannels and output microchannels and the relative volumetric flow rates from the input microchannels and output microchannels.

In some embodiments of the present invention, the input microchannel is connected to a pump (612) to control the flow of sample and reagents into the microfluidic channel. Conventional fluid pumps capable of producing desired shear stress in a device are suitable for use in some embodiments of the present invention. Nonlimiting examples of pumps include syringe pumps, peristaltic pumps, and vacuum sources. In some embodiments, pumps are coupled to the devices using conventional methods. The device may be configured for substantially constant shear stress in any given channel or variable shear stress in a given channel. One of ordinary skill in the art will know how to select and configure a pump for use in the present invention based on the volume and type of fluid to be processed as well as the desired fluid flow rate.

In embodiments, the device of the present invention includes a chaotic mixer. Conventional chaotic mixers are suitable for use in some embodiments of the present invention. In some embodiments, the flow layer has a textured surface that causes chaotic flow in the microfluidic channel. The chaotic flow increases the probability that the biological cells will come into contact with the nanostructured surface region of the substrate, thereby increasing the probability that the binding agents on the nanostructured surface regions will interact and bind to target biological cells in the sample. In some embodiments, the textured surface has a plurality of structures orientated relative to a principle direction of fluid flow that mix the circulating fluid. The textured surfaces may be formed in a variety of geometrical shapes, including for example, rectangular, circular, and parabolic. The shapes may be combined into a periodic or random arrangement. In some embodiments, the shapes may include a plurality of chevron-shapes that form a herring-bone pattern. As used herein, the term "herring-bone pattern" has its normal meaning of columns (e.g., two) of short parallel lines with all the lines in one column sloping one way and lines in adjacent column sloping the other way. Additional details about the patterns that may be formed in the textured surfaces to facilitate fluid mixing are described in U.S. Published Patent Application 2004/0262223, titled "LAMINAR MIXING APPARATUS AND METHODS," by Stook et al.

In some embodiments, devices of the present invention are fabricated using conventional techniques. The fabrication techniques employed will depend on the material used to make the device. Nonlimiting examples of fabrication techniques include molding, photolithography, electron beam lithography, soft lithography, electroforming, and machining. Nonlimiting examples of materials include glass, quartz, polymers (e.g., polystyrene, silicones such as polydimethylsiloxane (PDMS), epoxy, polymethylmethacrylate, urethanes, polysaccharide, polylactide, and polytetrafluoroethylene (Teflon)), silicon and other semiconductors, and metals (e.g., aluminum, titanium, and steel). The material may also be an inorganic oxide (e.g., zinc oxide, silicon oxide, titanium oxide, and aluminum oxide).

In some embodiments of the present invention, a microfluidic device is implemented by soft lithography. For example, a layer of polydimethylsiloxane (PDMS) can be applied to a substrate that has a desired pattern. The layer can be coated with resist, exposed to a light pattern, and etched to create structures to form fluid channels, for example, in a predefined pattern. Successive steps of coating, exposing, and etching can be used to create more complex structures.

3. METHODS OF USE

In embodiments, the devices of the present invention are employed to isolate rare cells from a sample. In some embodiments, the rare cells are circulating tumor cells from peripheral blood. In other embodiments, the rare cells are organisms found in peripheral blood (e.g., bacteria, viruses, protists, and fungi). In further embodiments, the rare cells are nonhemopoietic cells not normally found in blood (e.g., endothelial cells or fetal cells), and even cells of hemopoietic origin (e.g., platelets, sickle cell red blood cells, and subpopulations of leukocytes).

Cancers that may be detected using devices according to embodiments of the present invention include prostate, lung, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor. In some embodiments, the binding agents are anti-epithelial-cell adhesion molecule antibodies (anti-EpCAM antibodies). EpCAM provides specificity for CTC capture from unfractionated blood as it is frequently overexpressed by carcinomas of lung, colorectal, breast, prostate, head and neck, and hepatic origin, and can therefore provide clinical and diagnostic information relevant to tumors, even those considered clinically localized.

In addition to methods of isolating biological cells from a sample, some embodiments of the present invention provide methods in which the isolated cells may be used to provide additional information. In embodiments, cells isolated using the methods and devices of the present invention can be further assayed using additional in vitro assays. In some embodiments, cells that are isolated using the methods and devices of the present invention are counted. Conventional methods for counting cells can be used in some embodiments, including for example, optical, e.g., visual inspection, automated counting, microscopy based detection; FACS; and electrical detection, e.g., Coulter counters. Cell counting can be useful for diagnosing disease, monitoring the progress of disease, and monitoring or determining the efficacy of a treatment.

In some embodiments, cells isolated using the methods and devices of the present invention are subjected to immunocytochemical analysis by flowcytometry or other analytical platforms. Such analysis facilitates diagnosis and provides important information to the clinician.

In some embodiments, cells isolated using the methods and devices of the present invention can be lysed, and one or more properties of the cells, or portions thereof, can be measured. Nonlimiting examples of biological properties that can be measured in lysed cells include mRNA expression, protein expression, and DNA quantification. Additionally, in some embodiments, the cellular DNA can be sequenced, or certain sequence characteristics (e.g., polymorphisms and chromosomal abnormalities) can be identified using conventional techniques, e.g., FISH or PCR. In some embodiments, cells are lysed while still bound to the device. The ability to lyse cells on the device and obtain useful genetic information is made possible by the high purity of samples obtained using devices and methods according to some embodiments of the present invention.

In some embodiments, cells isolated by the methods of the present invention are assayed without lysis. Nonlimiting examples of methods for assaying non-lysed cells include using extracellular or intracellular stains; observing morphology or growth characteristics in various media; and identifying biomarkers on the cellular surface. In further embodiments, the isolated cells are cultured to obtain an enriched population of the isolated cells before use in subsequent in vitro assays.

In some embodiments of the present invention, information that can be obtained from the isolated cells includes identification or enumeration of particular genomic DNA, cDNA, or mRNA sequences; identification or enumeration of cell surface markers (e.g., CD133, CD44, CD24, epithelial-specific antigen (ESA), Nanog, and BMI1 on cancer stem cells); and identification or enumeration of proteins or other intracellular contents that are indicative of the type or presence of a particular tumor. In embodiments, CTCs may be analyzed to determine the tissue of origin, the stage or severity of disease, or susceptibility to a particular treatment.

In some embodiments, the methods and devices of the present invention are used to assess residual cancer cells in circulation following medical, radiation, or surgical treatment to eradicate the tumor. In further embodiments, the methods and devices of the present invention are performed periodically over a course of years to assess the patient for the presence and number of tumor cells in the circulation as an indicator of occurrence, recurrence and/or progression of disease.

Also provided in some embodiments of the present invention are kits for carrying out the methods described herein. In embodiments, the kit contains a device of the present invention. In some embodiments, the kit contains reagents for use with the device of the present invention. In further embodiments, the kit includes instructions for taking a sample from a mammalian subject (e.g., body fluid), and using the kit to diagnose cancer in a mammalian subject, or monitoring the effect of therapy administered to a mammalian subject having cancer.

Embodiments of the present invention can be further understood by reference to the following non-limiting examples. It will be apparent to those of ordinary skill in the art that many modifications, both to materials and methods, may be practiced without departing from the scope of the present disclosure.

EXAMPLES

It is understood that the examples and embodiments described herein are for illustrative purposes only and that various modifications or changes in light thereof will be suggested to persons of ordinary skill in the art and are to be included within the spirit and purview of this application.

Example 1

Preparation and Surface Modification of SiNW Substrates

Nanostructured cell-capture substrates were prepared as follows. First, densely packed silicon nanowires (SiNWs) with diameters between 100-200 nm were introduced onto silicon wafers (e.g., 1 cm×2 cm) using a wet chemical etching method (FIG. 2A). The surface of the silicon substrate was treated to become hydrophilic. The silicon wafer was sonicated in acetone and ethanol at room temperature for 10 and 5 minutes, respectively, to remove contamination from organic grease. Then, the degreased silicon substrate was heated in boiling Piranha solution (4:1 (v/v) $H_2SO_4$/$H_2O_2$) and RCA solution (1:1:5 (v/v/v) $NH_3$/$H_2O_2$/$H_2O$) for 1 hour each, and the silicon substrate was rinsed several times with deionized (DI) water. The clean silicon substrate was treated by a wet etching process. A Teflon vessel was used as the container, and an etching mixture consisting of DI water, HF, and silver nitrate was used at room temperature. The concentrations of HF and silver nitrate were 4.6 and 0.2 M, respectively. The etching duration was variable, depending on the required length of the nanowires. After etching, the substrate was immersed in boiling aqua regia (3:1 (v/v) HCl/$HNO_3$) for 15 minutes to remove the silver film. Finally, the substrate was rinsed by DI water, dried by nitrogen, and was ready for surface modification. The lengths of these chemically etched SiNWs can be controlled by applying different etching times. As a result, we were able to obtain a series of SiNW substrates with SiNW lengths varying from 1 to 25 μm (FIG. 2C). After the preparation of SiNW substrates, NHS-Maleimide chemistry (FIG. 2B) was employed to introduce streptavidin onto the surfaces of the SiNWs. The substrate was modified with 1% (v/v) 3-mercaptopropyl trimethoxysilane in ethanol at room temperature for 12 hours or with 4% (v/v) 3-mercaptopropyl trimethoxysilane in ethanol at room temperature for 45 minutes. The substrate was then treated with the coupling agent N-ymaleimidobutyryloxy succinimide ester (GMBS, 0.25 mM) for 30 mM, resulting in GMBS attachment to the substrate. Next, the substrate was treated with 10 μg/ml of streptavidin at room temperature for 30 minutes, leading to immobilization onto GMBS. The substrate was flushed with 1×PBS to remove excess streptavidin, and the streptavidin-coated SiNW substrate was stored in 4° C. in the presence of PBS buffer (pH=7.2) for up to 6 months. Biotinylated anti-EpCAM (R&D) was freshly introduced onto the streptavidin-coated substrate prior to use in cell-capture experiments.

Example 2

Comparison of Morphologies of Cells Captured on SiNW Substrates and Flat Substrates The nanoscale cell/substrate interactions were visualized using scanning electron microscope (SEM). In order to maintain the morphologies of the substrate-immobilized cells, the samples were processed by glutaraldehyde fixation, osmium tetroxide treatment, and dehydration. Briefly, cells were fixed with 1.5-4% glutaraldehyde buffered in 0.1 M sodium cacodylate (4° C., 1 hr) after a 24 hour incubation on substrates. Cells were then post-fixed in 1% osmium tetroxide for 1 hour and 1% tannic acid was used as a mordant. Samples were dehydrated through a series of alcohol concentrations (30%, 50%, 70% and 90%), stained in 0.5% uranyl acetate, and followed by further dehydration (96%, 100% and 100% alcohol). The final dehydration was in hexamethyldisilazane (HMDS) followed by air drying. Once dry, the samples were sputter coated with gold before examination with a Hitachi S800 field emission SEM at an accelerating voltage of 10 keV.

The cells were also visualized using fluorescence microscopy. Control samples were prepared by spiking DiD stained MCF7 breast cancer cells into rabbit blood at cell densities of 1000-1250, 80-100 and 5-20 cells/mL. 25 µL of biotinylated anti-EpCAM (10 µg/mL in PBS with 1% (w/v) BSA and 0.09% (w/v) sodium azide) was added onto a 1 cm×2 cm substrate and incubated for 30 minutes. The substrate was washed with PBS. 1 mL of sample was added onto a substrate and incubated for 45 minutes (37° C., 5% $CO_2$). The substrate was washed with PBS and the cells captured on the substrate were fixed with 4% paraformaldehyde (PFA) in PBS for 20 minutes. To stain and visualize captured cells, 0.9 mL of 0.2% Triton X-100 in PBS was added to the substrate and incubated for 10 minutes. A DAPI solution (1×DAPI reagent in 1 mL of DI water) was then added to the substrate and incubated for 5 minutes. The substrate was washed with PBS, and the substrate was inverted onto a standard cover glass. Cells were imaged and counted using a Nikon TE2000 fluorescence microscope. Color, brightness, and morphometric characteristics including cell size, shape, and nuclear size were employed to identify potential CTCs and exclude cell debris and non-specific cells. Cells that showed dual stains (red: $DiD^+$ and blue: $DAPI^+$) and had certain phenotypic morphological characteristics were scored as CTCs, and $DAPI^+$ cells were scored as non-specific cells.

Figure 3C:
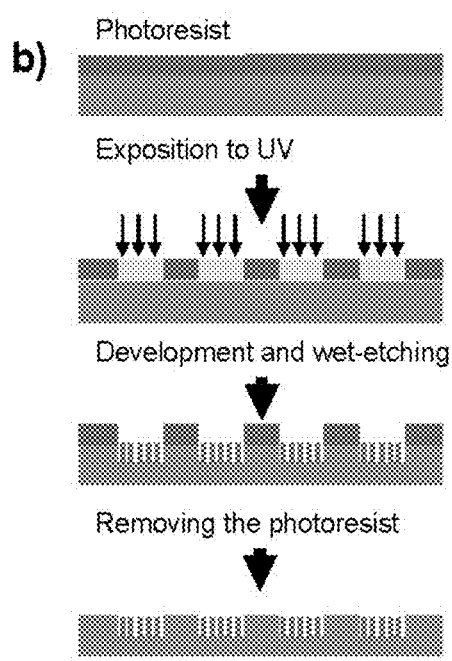

As shown in the right of FIG. 3A, the cells captured on flat Si substrates show significantly different morphologies as compared to cells captured on SiNW substrates. The insets in FIG. 3A are the typical morphologies of cells captured on flat Si substrates (top) and SiNW substrates (bottom). On flat substrates, there are lamellipodia linked lamellas surrounding the central part of cell (usually including nucleus and perinuclear organelles). These results suggest that cells begin to spread once they associate with the flat Si substrates, although the cells have difficulty attaching onto the flat Si substrates. In contrast, a lot of filopodia protruding from cells attach onto nanowires in three dimensions (3D) on the SiNW substrates, with either their top or middle "grasping" the nanowires. Also, the filopodia are nanoscale in size (approximately 100-150 nm) like the lateral dimension of the SiNWs. Although the SiNWs are immobile, cell surface components can arrange themselves, resulting in more intimate local interactions between cells and substrates. Therefore, SiNWs contribute to cell capture and account for the different morphologies observed with cells associated with flat Si substrates and SiNW substrates.

We also confirmed these results using Daudi B cells (i.e., cancerous B cells) as the target cells and nanostructures coated with anti-CD20 to capture the Daudi B cells. The results are shown in FIG. 3B and are consistent with the results observed with MCF7 breast cancer cells.

Figure 3D:
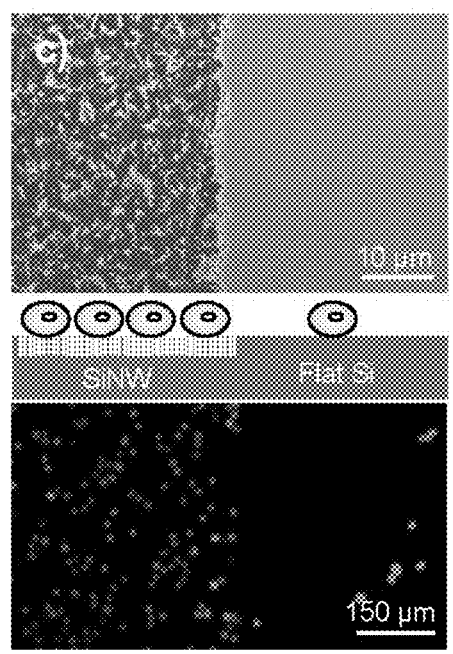
FIG. 3D shows an SEM image of patterned substrates before cell capture (top) and fluorescence images of cells captured on patterned substrates (bottom).

We further compared the binding efficiency of SiNW substrates with flat Si-substrates when placed in close proximity Photolithography was used to apply a pattern onto the silicon substrate (the left panel in FIG. 3C) in combination with a chemical etching process. We made the patterned substrate with and without nanowires (top of FIG. 3D). After a similar process of surface modification and cell capture as described above, the patterned substrate were observed under a fluorescence microscope. In these experiments, we used MCF7 breast cancer cells and nanostructures coated with anti-EpCAM. As shown in the bottom of FIG. 3D, significantly fewer cells were observed on the flat area as compared to the nanowire area. These results are consistent with the result obtained above, and provide further evidence that nanowire-based surfaces can exhibit an amplified effect on cell capture as compared with flat surfaces.

Example 3

Influence of Capture Time on Cell-Capture Efficiency

Figure 4A:
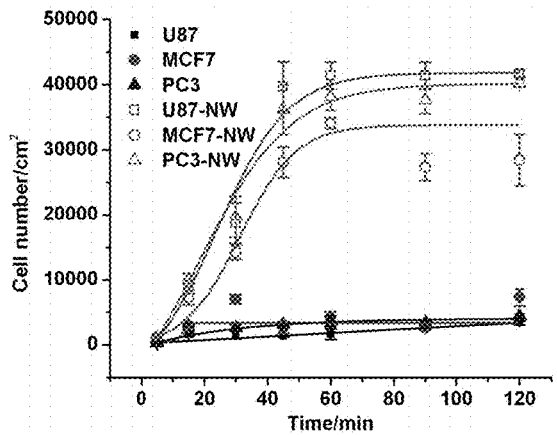
FIGS. 4A and 4B show the effects of capture times and SiNW length on the capture efficiency of SiNW substrates, which are embodiments of the present invention.

To determine the minimum time required to achieve maximum cell capture, we examined cell capture performance of both of the 10 µm SiNWs and flat Si-substrates (with anti-EpCAM coating) at different incubation times. Three EpCAM-expressed cancer cells (i.e., MCF7, U87 brain cancer cells and PC3 prostate cancer cells) were tested. FIG. 4A summarizes the correlation between incubation time and the number of substrate-immobilized cells. In the presence of SiNW substrates, maximum cell capture was achieved at a 45 minute incubation time regardless of the types of cells examined. At the 45 minute time point, the 10 µm SiNWs exhibit up to 10 times better cell-capture efficiency as compared to the flat Si-substrates. Continuous increase of cell numbers was observed for the flat Si-substrates; however, overall cell capture numbers were significantly lower for flat Si-substrates than those observed for the SiNW substrates.

Figure 5:
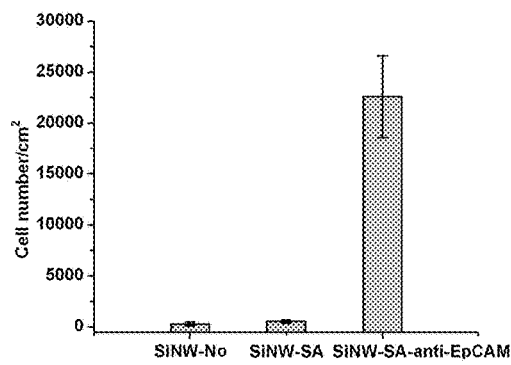
FIG. 5 compares the cell capture performance of three different substrates: SiNW substrate without any surface modification (SiNW-No), SiNW substrate with streptavidin coating (SiNW-SA) and SiNW substrate modified with anti-EpCAM (SiNW-SA-EpCAM).

We assessed whether this high capture yield comes from non-specific interaction of SiNWs by performing similar cell capture experiments on three different substrates: SiNW substrate without any surface modification (SiNW-No), SiNW substrate with streptavidin coating (SiNW-SA), and SiNW substrate modified with anti-EpCAM (SiNW-SA-EpCAM). The number of cells captured on SiNW-No and SiNW-SA substrates were less than 5% of that on the SiNW substrate (FIG. 5). Therefore, high yield of cell capture on SiNW substrates is due to the cooperative effect of physical local interactions between SiNWs and cell surface components and chemical recognition between anti-EpCAM and EpCAM on cell surface.

Example 4

Influence of SiNW Length on Cell-Capture Efficiency

Figure 4B:
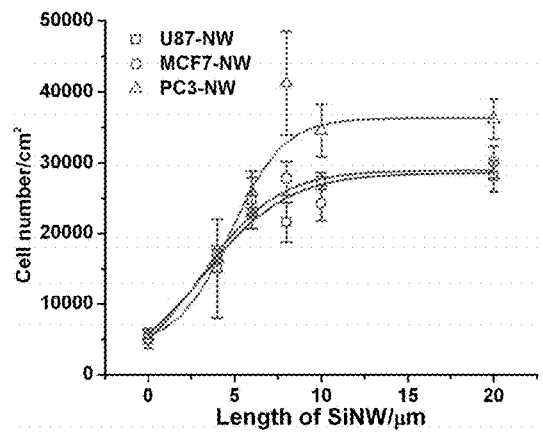

We utilized a series of SiNW substrates with SiNWs lengths of 4, 6, 8, 10, and 20 µm in the cell-capture experiments. Samples containing cancer cell lines (i.e., MCF7, U87 brain cancer cells, or PC3 prostate cancer cells) were statically incubated on SiNW substrates and flat substrates. Anti-EpCAM was coated on both substrates, and as shown in FIG. 4B, increasing the longitudinal dimension of the SiNW resulted in increasing the number of cells captured. When the lengths of the SiNWs were longer than 6 µm, maximum cell capture efficiency was achieved.

Example 5

Static Capture of CTCs from Spiked Whole Blood Sample

We tested the ability of our device to perform static cell capture. Artificial CTC-containing blood samples were prepared by spiking enhanced green fluorescent protein (EGFP)-expressed U87 cells into rabbit blood with cell densities of 1000, 100 and 5 cells/mL of blood. The spiked samples were incubated on 10 μm EpCAM-coated SiNW substrates for 45 minutes. As shown in Table 1, our approach has a high capture yield (>40%), high specificity (>40%) and high sensitivity (>90%). These results indicate that the device of the present invention performs significantly better than the current leading technology, i.e., the immunomagnetic-bead method, which has very low sensitivity (~20-60%) and low specificity (~0.1%).

TABLE 1

| | Range of number of CTCs/$10^9$ blood cells | | |
| --- | --- | --- | --- |
| | 1000~1250 | 80~120 | 5~20 |
| Capture yield | 55% | 40% | 65% |
| Specificity | 64% | 57% | 44% |
| Sensitivity | 100% | 100% | 92% |

Example 6

Preparation of the Chaotic Mixing PDMS Layer

We generated a microfluidic device of the present invention having a flow layer that produces chaotic mixing. (See FIGS. 6A and 6B). The chaotic mixing PDMS layer was fabricated by stand soft-lithography technology. First, we fabricated a silicon mold with positive patterns, having a two layer SU-8 pattern. The bottom layer is the main microchannel (100 um height and 2 mm width) and the top layer is the herring-bone (chaotic mixing) microchannel (25 um height). The herring-bone structure is similar to rifling in a gun barrel, which can make an anisotropic resistance to viscous flows. After pouring the PDMS mixture and baking it for a few hours, we get the PDMS layer with a herring-bone structure on the top of microchannels. After an inlet and outlet is punched into the PDMS layer, the 1-3 μm thick adhesive PDMS layer was transferred to the PDMS block through contact printing, followed by direct attachment onto the anti-EpCAM-coated SiNW substrate to give an assembled device.

Example 7

The Influence of Flow Rate on Cell-Capture Efficiency

To determine the optimized flow rate required to achieve maximum cell capture number in the microfluidic device, we spiked breast cancer cells (i.e., MCF7) into PBS at 100 cells/mL and captured the spiked cancer cells. The microfluidic device was connected to a sample bottle. Biotinylated anti-EpCAM (10 μg/mL in PBS with 1% (w/v) BSA and 0.09% (w/v) sodium azide) was loaded into the sample bottle such that the microfluidic device was filled with the solution. The biotinylated anti-EpCAM solution was incubated for 30 minutes, and the microfluidic device was then washed with PBS. 1 mL of sample was pressured through the microfluidic chip at a desired flow rate, followed by washing with PBS. The microfluidic device was filled with 4% paraformaldehyde (PFA) in PBS for 20 minutes in order to fix the cells captured on the substrate. To stain and visualize captured cells, the PFA was replaced with 0.2% Triton X-100 in PBS for 10 minutes followed by DAPI solution (1×DAPI reagent in 1 mL of DI water) for 5 minutes. The microfluidic device was washed with PBS, and the microfluidic layer was separated from the substrate. The substrate was inverted onto a standard cover glass for imaging.

Figures 7A, 7B, 7C:
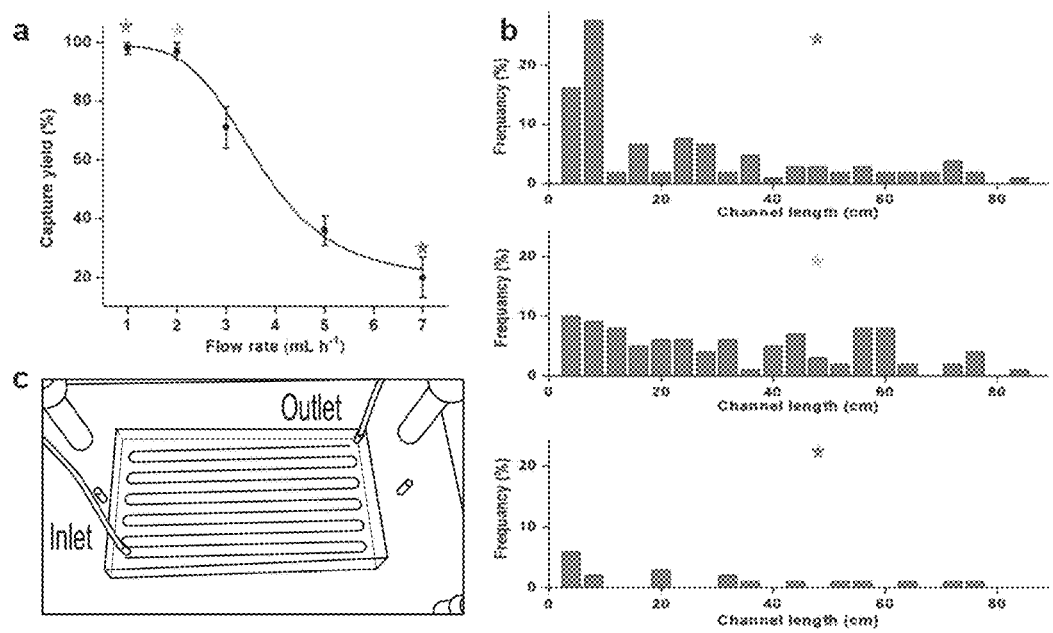
FIGS. 7A-7C show the effects of flow rate on cell capture in a microfluidic device according to an embodiment of the present invention.

The calculated capture efficiency was above 90% and decreased significantly at flow rates above 3 mL/hour (FIG. 7A), presumably owing to increased shear stress. The efficiency of capture was not enhanced at flow rates less than 1 mL/hour, leading us to select a flow rate of 1-2 ml/hour for subsequent studies. FIG. 7A summarizes the correlation between flow rates and capture yields.

Example 8

Effect of EpCAM Expression Level on Different Cancer Cell Lines

Figure 8:
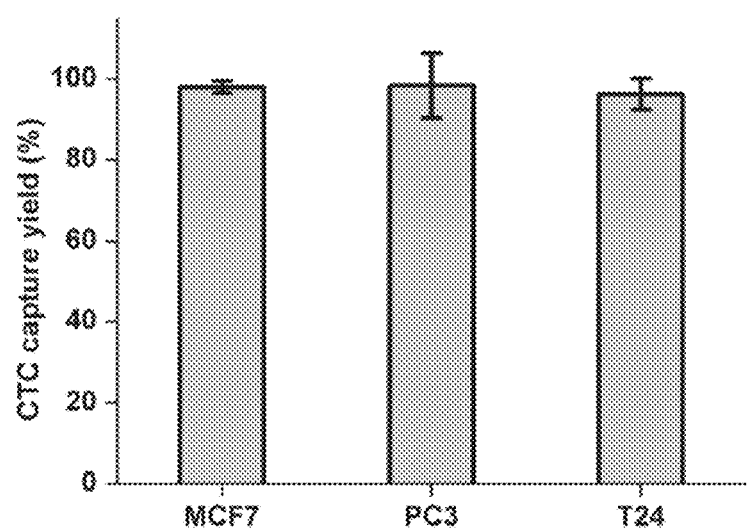
FIG. 8 shows capture yields of PBS spiked with 100 cells per mL of three different cancer cell lines: breast (MCF7), prostate (PC3), and bladder (T-24), in a microfluidic device according to an embodiment of the present invention.

To determine the effect of EpCAM expression on CTC capture efficiency with a microfluidic device according to an embodiment of the present invention, we compared the capture yields among three cancer cell lines with varied EpCAM expression, including breast cancer MCF-7 cells, with >500,000 antigens per cell; prostate cancer PC3 cells, with approximately 50,000 antigens per cell; and bladder cancer T-24 cells, with approximately 2,000 antigens per cell. Each cell line was spiked into PBS at a concentration of 100 cells/mL. Despite the varying levels of EpCAM expression on each cell line, mean capture yield was >90% in all cases (FIG. 8). These results may be due to the amplified cell-substrate interactions between cells and SiNW substrates in a microfluidic device.

Example 9

Capture CTCs from Spiked Sample with a Microfluidic Device

Figure 9:
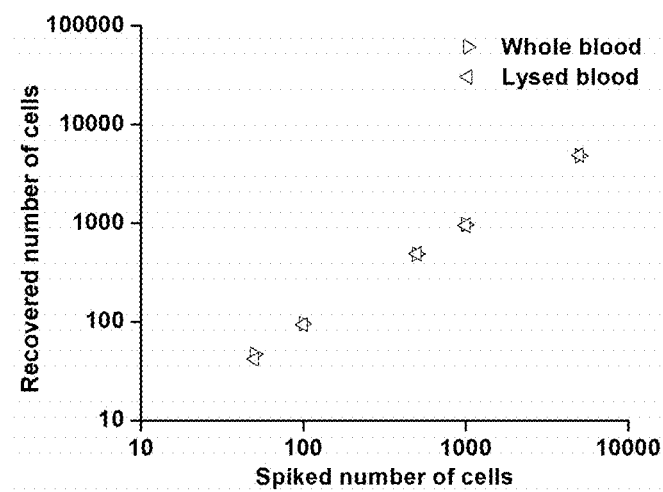
FIG. 9 shows the capture efficiency for various target cell concentrations, comparing whole blood to lysed blood samples, in a microfluidic device according to an embodiment of the present invention. The plot represents number of cells spiked versus cells recovered.

To test the cell capture efficiency of the microfluidic device, artificial CTC-containing blood samples were prepared by spiking DiD-stained MCF7 (breast cancer cell line) into healthy donor blood at cell densities of 5000, 1000, 500, 100 and 50 cells/mL of blood. The spiked samples were incubated on 10 μm EpCAM-coated SiNW substrates for 45 minutes. As shown in FIG. 8, our microfluidic device shows a high capture yield (>90%), which is much higher than the immunomagnetic-bead method. To assess the potential spatial obstacle of red blood cells in the flow path, these studies were repeated using lysed blood from healthy donors. Using whole blood and lysed samples, we obtained similar results (FIG. 9).

Figures 10A, 10B, 10C, 10D:
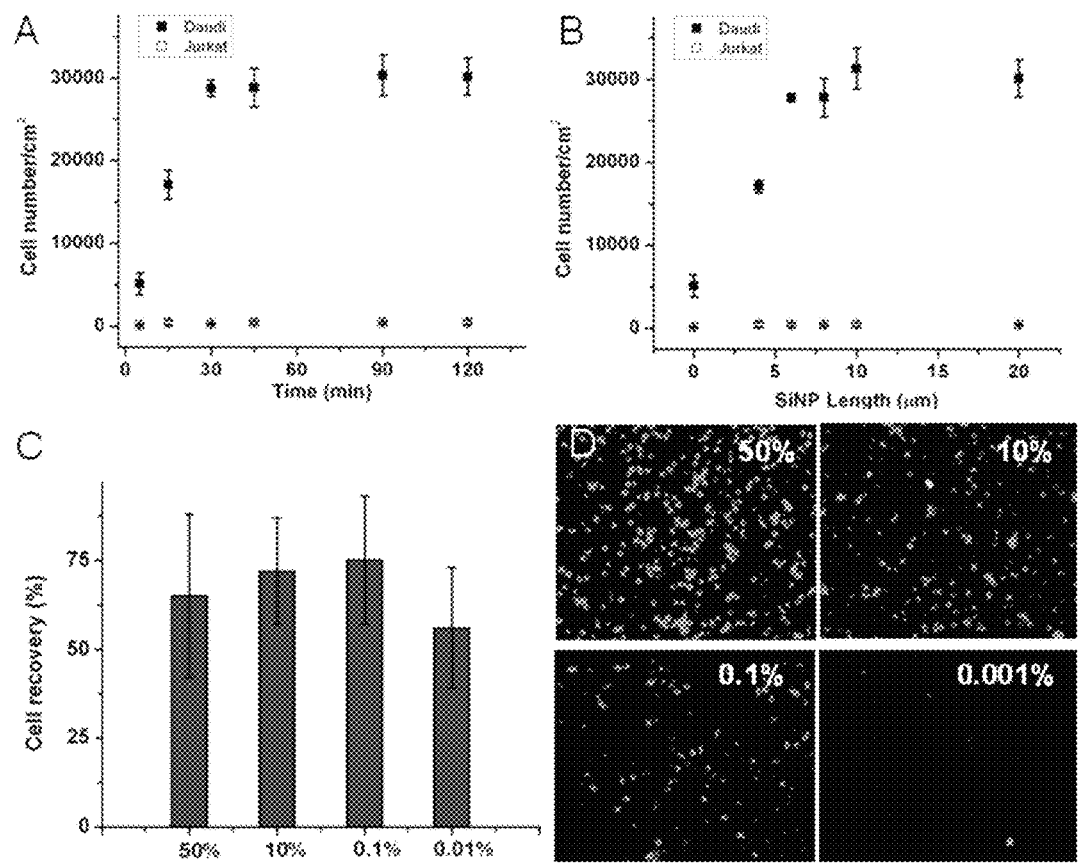
FIGS. 10A-10D show the effects of capture time and SiNW length on capture efficiency of a microfluidic device according to an embodiment of the present invention.

We also tested the effect of capture time and SiNW length on the capture efficiency of the microfluidic device. To determine the minimum time required to achieve maximum cell capture, we examined cell capture performance of both of the 10 μm SiNWs (with anti-EpCAM coating) at different incubation times. Daudi B cells (i.e., cancerous B cells) and Jurkat cells (i.e., cancerous T cells) were tested on anti-CD20 coated substrates in the microfluidic device. FIG. 10A summarizes the correlation between incubation time and the number of substrate-immobilized cells. In the presence of SiNW substrates, maximum cell capture was achieved at a 30 minute incubation with Daudi B cells. In contrast, cell capture was not observed with Jurkat cells lacking CD20 on the cell surface.

To assess the correlation between SiNW length and capture efficiency, we utilized a series of SiNW substrates with SiNWs lengths of 4, 6, 8, 10, and 20 µm in the cell-capture experiments. Daudi B cells and Jurkat cells were tested, and as shown in FIG. 10B, increasing the longitudinal dimension of the SiNW resulted in increasing the number of cells captured. Maximum cell capture efficiency was achieved when the length of SiNW was 6 µm.

Example 10

Comparison of Captured CTC Number Between Our Microfluidic Chip and Cellsearch™ Technology After opimization of experimental parameters, we carried out a clinical study using CTC blood samples collected from metastatic prostate cancer patients in collaboration with the Department of Urology at UCLA under the UCLA IRB approval (IRB #09-03-038-01). We first examined the ability of a device according to an embodiment of the present invention to capture CTCs under static binding conditions. Briefly, Blood samples were drawn from patients with advanced solid-stage tumors (as approved by IRB) and collected into vacutainer tubes containing ETDA. 25 µL of biotinylated anti-EpCAM (10 µg/mL in PBS with 1% (w/v) BSA and 0.09% (w/v) sodium azide) was added onto a 1 cm×2 cm substrate and incubated for 30 minutes. The substrate was washed with PBS, and 1 mL of sample was added onto the substrate and incubated for 45 minutes (37° C., 5% $CO_2$). The substrate was washed with PBS and the captured cells fixed with 4% paraformaldehyde (PFA) in PBS for 20 minutes.

A 3-parameter immunocytochemistry protocol (for parallel staining of DAPI, FITC-labeled anti-CD45 and PE-labeled anti-cytokeratin (CK)) was applied to stain the immobilized cells. For example, 200 µL of 0.3% Triton X-100 in PBS was added to the substrate and incubated for 30 minutes. 200 µL of blocking solution (5% normal goat serum, 0.1% Tween 20, 3% BSA in PBS) was added to the substrate and incubated for one hour at room temperature. Next, 200 µL of fluorophore-labeled antibody solution (20 µL/1 mL initial concentration) was added to the substrate and incubated in the dark at 4° C. overnight. The substrate was washed with PBS, and DAPI solution (10 µg/mL) was added and incubated for 5 minutes. The substrate was washed with PBS, and the substrate was inverted onto a standard cover glass for imaging.

We also tested the samples in a microfluidic device according to an embodiment of the present invention. The microfluidic device was connected to a sample bottle. Biotinylated anti-EpCAM (10 µg/mL in PBS with 1% (w/v) BSA and 0.09% (w/v) sodium azide) was loaded into the sample bottle such that the microfluidic device was filled with the solution. The biotinylated anti-EpCAM solution was incubated for 30 minutes, and then washed with PBS. 1 mL of patient sample was pressured through the microfluidic chip at a flow rate of 1 mL/hour. The microfluidic device was washed with PBS, followed by 4% paraformaldehyde (PFA) in PBS for 20 minutes in order to fix the captured cells. To stain and visualize captured cells, PFA was replaced with 0.2% Triton X-100 in PBS for 10 minutes followed by fluorophore-labeled antibody solution (20 µL/1 mL initial concentration). The microfluidic device was incubated in the dark at 4° C. overnight. The microfluidic device was then washed with PBS, and DAPI solution (1×DAPI reagent in 1 mL of DI water) was added and incubated for 5 minutes. The microfluidic device was washed with PBS, and the microfluidic layer was separated from the substrate. The substrate was inverted onto a standard cover glass for imaging According to the signal thresholds and size/morphology features established for model cells, CTCs were clearly distinguished from the background immune cells. Since only 1.0 mL of patient blood is required for each CTC capture study, we were able to perform 3 measurements on each patient blood sample we received. FIGS. 11A-11C shows the results of CTC-capture experiments using our device under static conditions (FIG. 11B), using our device under fluid conditions (FIG. 11C), and using the CellSearch™ technology (FIG. 11A). Our devices, under static and fluid conditions, were able to identify CTC positive patient samples, where the CellSearch™ technology failed to register any CTC counts.

Example 11

Reagents

Nonlimiting examples of reagents suitable for use in practicing embodiments of the present invention include the following:
1. Oriented prime grade silicon wafers, p-type, resistivity of ca. 10-20 ohm-cm (Silicon Quest Int'l). Stored at room temperature.
2. Photoresist (PR) AZ 5214 (AZ Electronic Materials USA Corp.)
3. Developer AZ 400K (AZ Electronic Materials USA Corp.)
4. Photoresist SU8-2100 (MicroChem Corp. USA.)
5. Photoresist SU8-2025 (MicroChem Corp. USA.)
6. Developer SU8 (MicroChem Corp. USA.)
7. Ethanol, >99.5% (Sigma-Aldrich Co). Stored at room temperature.
8. Sulfuric acid, 98% (Sigma-Aldrich Co, #32050-1). Stored at room temperature.
9. Hydrogen peroxide, 30% (Sigma-Aldrich Co, #31698-9). Stored at room temperature.
10. Hydrofluoric acid, 48% wt. % in $H_2O$ (Sigma-Aldrich Co, #339261-100 mL). Stored at room temperature.
11. Silver nitrate, >99.8% (Sigma-Aldrich Co, #56506-5G). Stored at room temperature.
12. Acetone, ACS reagent, SpectroGrade 99.5% (Fisher Scientific, #AC40010-0040). Stored at room temperature.
13. Isopropanol, ACS reagent, SpectroGrade 99.5% (Fisher Scientific, # AC41279-5000). Stored at room temperature.
14. 3-Mercaptopropyl trimethoxysilane, 95% (Sigma-Aldrich Co, #175617-25G). Stored at room temperature.
15. N-y-maleimidobutyryloxy succinimide ester (4-Maleimidobutyric acid N-hydrosuccinimide, GMBS), >98% HPLC (Sigma-Aldrich Co, #63175-25MG-F). Stored at room temperature.
16. Streptavidin, 1 mg/mL (Invitrogen, #SNN1001). Stored in single use aliquots at −20° C.
17. Glutaraldehyde E. M. grade, 3% (Polysciences). Stored at room temperature.
18. Cacodylic acid sodium salt trihydrate (Sigma Aldrich, #C0250-10 g). Stored at room temperature.
19. Osmium tetroxide, ACS reagent, >98% (Sigma Aldrich, #419494-250 mg). Toxic! Store at room temperature.
20. Tannic acid (Electron Microscopy Sciences). Storedat room temperature.
21. Uranyl acetate (Electron Microscopy Sciences). Storedat room temperature.
22. Hexamethyldisilazane (HDMS) (Sigma, #H4875-100 mL). Toxic! Stored at room temperature.
23. Trimethylsilyl chloride (TMSCI, >98%, Alfa Aesar, # MFCD00000502)
24. Polydimethylsiloxane (PDMS, GE RTV 615)

25. Breast cancer cell line, MCF7 (American Type Culture Collection)
26. Dulbecco's Modified Eagle's Medium (DMEM, 1×), liquid (high glucose), (Invitrogen, #11965-118)
27. Fetal bovine serum (FBS), standard (Fisher Scientific, #BW14-502F). Stored at −20° C.
28. Penicillin-Streptomycin, 100× (Fisher Scientific, #ICN1670049). Stored at −20° C.
29. Citrated whole rabbit blood (Colorado Serum Company)
30. Vybrant® DiD cell-labeling solution (Invitrogen, #11330-057). Stored at 4° C.
31. Dulbecco's phosphate buffered saline (PBS), (Invitrogen, #14190250) Stored at 4° C.
32. Biotinylated anti-human EpCAM/TROP1 antibody (Goat IgG, R&D) diluted to 10 µg/mL, following the R&D product manu. Stored in single use aliquots at −20° C.
33. Lab-Tek chamber slides, 4 well glass, sterile (Thermo Fisher Scientific, #177399). Stored at room temperature.
34. Cytokeratin anti-cytokeratin PE (CAM5.2, conjugated with phycoerythrin) (BD Biosciences, #347204) diluted to 20 µg/mL in PBS. Stored in single use aliquots at −20° C.
35. FITC anti-human CD45, Ms IgG1, clone H130 (BD Biosciences, #555482) diluted to 20 µg/mL in PBS. Stored in single use aliquots at −20° C.
36. 1×PBS buffer (rinsing agent). Store at 4° C.
37. 1% DAPI in 1×PBS (nucleic staining agent). Stored at 4° C.
38. 4% paraformaldehyde in 1×PBS (fixing agent). Stored at 4° C.
39. Bovine serum albumin (BSA), (Sigma). Stored at 4° C.
40. Triton X-100. Stored at 4° C.

Example 12

Methods for Practicing Embodiments of the Present Invention

Nonlimiting examples of methods for making and practicing embodiments of the present invention include the following:
1. Cut silicon wafer into pieces of silicon substrates having an area of 1 cm×2 cm.
2. Ultrasonicate the cut silicon substrate in acetone for 10 min. at room temperature and dry it under nitrogen gas. Next, ultrasonicate substrate in ethanol for five minutes at room temperature and dry under nitrogen gas. These steps remove contamination (such v/as organic grease) from the silicon substrate.
3. To etch the silicon wafer surface, first heat the silicon substrate in boiling Piranha solution (4:1 (v/v) $H_2SO_4/H_2O_2$) for 1 hr. Then, heat substrate in boiling RCA solution (1:1:5 (v/v) $NH_3/H_2O_2/H_2O$) for 1 hr. Rinse the substrate five times with DI water. Next, place the silicon substrates in a Teflon vessel and etch substrate with etching mixture (4.6 M HF, 0.2 M silver nitrate in DI water) at 50° C.
4. Immerse substrate in boiling aqua regia (3:1 (v/v) $HCl/HNO_3$) for 15 min
5. Rinse substrate with DI water and dry under nitrogen gas.
1. Add 4% (v/v) 3-mercaptopropyl trimethylsilane in ethanol to the substrate, then leave the substrate in room temperature for 45 min
2. Treat substrate with 0.25 mM N-maleimidobutyryloxy succinimide ester (GMBS) and incubate for 30 min at room temperature.
3. Treat substrate with 10 µg/mL streptavidin (SA) and incubate for 30 minutes at room temperature.
4. Flush substrate with 1×PBS to remove excess streptavidin.
5. Store modified substrates at 4-8° C. for up to 6 months.
1. Allow cells to incubate on the substrates for 24 hours.
2. Fix cells with 4% glutaraldehyde buffered in 0.1 M sodium cacodylate and incubate cells for 1 hr at 4° C. Afterward, fix cells using 1% osmium tetroxide for 1 hr. Use 1% tannic acid as a mordant.
3. Dehydrate samples through a series of alcohol concentrations (30%, 50%, 70%, and 90%). After dehydrating, stain samples with 0.5% uranyl acetate. Further dehydrate the samples through a series of higher alcohol concentrations (96%, 100%, and 100%). Dehydrate samples for the final time in hexamethyldisilazane (HMDS).
4. Air dry samples.
5. Once dry, sputter coat samples with gold and examine with a field emission SEM (accelerating voltage of 10 keV).
1. Stain MCF7 cells with DiD red fluorescent dye.
2. Prepare control samples by spiking stained MCF7 cells into rabbit blood with cell densities of 1000-1250, 80-100 and 5-20 cells/mL.
1. Place substrates into a size-matched 4-well Lab-Tek Chamber Slide. Drop 25 µL of biotinylated anti-EpCAM (10 µg/mL in PBS with 1% (w/v) BSA and 0.09% (w/v) sodium azide) onto a 1 cm×2 cm substrate. Incubate for 30 min. Wash with PBS.
2. Load 1 mL of control sample onto each substrate.
3. Incubate device setup for 45 min (37° C., 5% $CO_2$).
4. Gently wash substrate with PBS at least 5 times.
5. Fix cells captured on substrate with 4% paraformaldehyde (PFA) in PBS for 20 min
6. To stain and visualize captured cells, treat substrate with 0.9 mL of 0.2% Triton X-100 in PBS and incubate for 10 min. Incubate substrate with a DAPI solution (1×DAPI reagent in 1 mL of DI water) for 5 min Wash the substrate three times with PBS. Invert substrate onto a standard cover glass.
7. Image and count cells using a Nikon TE2000 fluorescence microscope.
8. Cells that show dual stains (red: DiD+ and blue: DAPI+) and meet the phenotypic morphological characteristics are scored as CTCs. Color, brightness, and morphometric characteristics including cell size, shape, and nuclear size are employed to identify potential CTCs and exclude cell debris and non-specific cells. Cell counts by DAPI+ only are non-specific cells.
9. These procedures should maximize the efficiency of blood sample preparation.
1. Place substrates into a size-matched 4-well Lab-Tek Chamber Slide. Drop 25 µL of biotinylated anti-EpCAM (10 µg/mL in PBS with 1% (w/v) BSA and 0.09% (w/v) sodium azide) onto a 1 cm×2 cm substrate. Incubate for 30 min Wash with PBS.
2. Blood samples drawn from patients with advanced solid-stage tumors (as approved by IRB) are collected into vacutainer tube containing the anticoagulant ETDA. Samples should be processed immediately after collection.
3. To capture cells, load 1 mL of patient sample onto each SiNP substrate. Incubate device setup for 45 min (37° C., 5% $CO_2$). Gently wash the substrate with PBS at least 5 times.

4. Fix cells captured on substrate by loading 200 µL of 4% paraformaldehyde (PFA) in PBS onto each substrate for 20 min at room temperature. Wash each substrate three times with PBS.
5. Permeabilize cells by treating each substrate with 200 µL of 0.3% Triton X-100 in PBS for 30 min at room temperature. Subsequently, wash each substrate three times with PBS.
6. Add 200 µL of blocking solution (5% normal goat serum, 0.1% Tween 20, 3% BSA in PBS) to each substrate and incubate for one hour at room temperature. Next, add 200 µL of fluorophore-labeled antibody solution (20 µL/1 mL initial concentration) to each substrate and incubate the substrate in the dark at 4° C. overnight. Wash with 200 µL PBS three times (First wash for 15 min at room temperature, second and third washes for 5 minutes at room temperature). Incubate substrate with DAPI solution (10 µg/mL) for 5 minutes. Wash each substrate 3 times with PBS.
7. Gently invert substrate, using tweezers, onto a cover glass to prepare for imaging.
1. Select fluorescent microscope settings.
    1.1. Optimized exposure times
        1.1.1. DAPI (blue) filter: 50 ms exposure time (background: ~1300)
        1.1.2. FITC (green) filter: 300 ms exposure time (background: ~1600)
        1.1.3. TRITC (red) filter: 100 ms exposure time (background: ~1300)
    1.2. Digitizer should be set to 1 MHz. Other settings will yield very high background in green filter.
2. Place sample on microscope and focus on edge of substrate. Once focused, switch filter to DAPI
    2.1. Starting in the upper right corner of the substrate, scan for nuclei that are approx. 7 to 20 µm in diameter at 4× or 10× magnification.
    2.2. Increase magnification to 10× or 20× when a putative cell has been located. Using a microscope mouse, check fluorescence intensity under DAPI, TRITC, and FITC fluorescence. Sample fluorescence intensity >2× background fluorescence intensity is scored as a positive result.
3. Cells that demonstrate dual staining (red: anti-cytokeratin PE$^+$ and blue: DAPI$^+$) and meet standard phenotypic and morphological characteristics should be scored as CTCs. Cells that show dual staining (green: anti-CD45 FITC$^+$ and blue: DAPI$^+$) should be excluded as lymphocytes/non-specific cells. Items that demonstrate staining in all three filters (green+ and red+ and blue+) should be excluded as cell debris.
1. Cleaning wafer: acetone, ethanol & DI water.
2. Drying wafer: blow dry wafers & put on hot plate 150° C. for 5 min
3. Pour AZ 5214 onto wafer.
4. Spin the wafer at 1000 rpm for 1 min
5. Soft bake wafers at 100° C. for 1 min
6. Expose wafers for UV for 56 mJ/cm$^2$.
7. Prepare developing solution: AZ 400K: water=1:3.
8. Develop AZ 5214 with the developing solution.
9. Blow dry the product.
10. Hard bake AZ 5214 at 100° C. for 5 min.
11. To etch the AZ 5214 patterned silicon wafer surface, place the silicon substrates in a Teflon vessel and etch substrate with etching mixture (4.6 M HF, 0.2 M silver nitrate in DI water) at 50° C.
12. Immerse substrate in boiling aqua regia (3:1 (v/v) HCl/HNO$_3$) for 15 min
13. Rinse substrate with DI water and dry under nitrogen gas.
1. Cleaning wafer: acetone, ethanol & DI water.
2. Drying wafer: blow dry wafers & put on hot plate 150° C. for 5 min
3. Pour SU8-2100 onto wafer.
4. Spin the wafer at 3000 rpm for 1 min
5. Soft bake wafers at 95° C. for 15 min
6. Expose wafers for UV for 320 mJ/cm$^2$.
7. Post bake wafers at 95° C. for 10 min
8. Develop SU8-2100 with the SU-8 developing solution.
9. Blow dry the product.
10. Hard bake SU8-2100 at 150° C. for 5 min.
11. Pour SU8-20250 onto wafer.
12. Spin the wafer at 2000 rpm for 1 min
13. Soft bake wafers at 95° C. for 8 min
14. Expose wafers for UV for 250 mJ/cm$^2$.
15. Post bake wafers at 95° C. for 5 min
16. Develop SU8-2025 with the SU-8 developing solution.
17. Blow dry the product.
18. Hard bake SU8-2025 at 150° C. for 10 min
1. Expose the silicon mold for microfluidic chip to TMSCI vapor for 10 min
2. Pour well mixed PDMS pre-polymer (GE RTV 615 A and B, total 20 g, mixing ratio A:B=10:1) onto the silicon mold.
3. Bake the pre-polymer at 80° C. for 48 h.
4. Peel PDMS layer off from the silicon mold and punch holes for inlet and outlet.
5. Clap the PDMS layer onto the Streptavidin-Coated SiNP Substrates to form a microfluidic chip.
1. Stain MCF7 cells with DiD red fluorescent dye.
2. Prepare control samples by spiking stained MCF7 cells into rabbit blood with cell densities of 1000-1250, 80-100 and 5-20 cells/mL.
1. Connect the microfluidic chip to the sample bottle. Load 25 µL of biotinylated anti-EpCAM (10 µg/mL in PBS with 1% (w/v) BSA and 0.09% (w/v) sodium azide) into the sample bottle. Fill full of the microfluidic chip with the solution. Incubate for 30 min. Wash with PBS.
2. Pressure 1 mL of artificial blood sample through the microfluidic chip at the desired flow rate.
3. Gently wash microfluidic chip with 100 µL PBS.
4. Fill full of the microfluidic chip with 4% paraformaldehyde (PFA) in PBS for fixing cells captured on substrate for 20 min.
5. To stain and visualize captured cells, replace the PFA with 0.2% Triton X-100 in PBS and incubate for 10 min
6. Replace the Triton X-100 with a DAPI solution (1×DAPI reagent in 1 mL of DI water) for 5 min
7. Wash the microfluidic chip with 200 µL PBS.
8. Unclap the microfluidic layer from substrate and invert substrate onto a standard cover glass.
9. Image and count cells using a Nikon TE2000 fluorescence microscope.
10. Cells that show dual stains (red: DiD+ and blue: DAPI+) and meet the phenotypic morphological characteristics are scored as CTCs. Color, brightness, and morphometric characteristics including cell size, shape, and nuclear size are employed to identify potential CTCs and exclude cell debris and non-specific cells. Cell counts by DAPI+ only are non-specific cells.
1. Connect the microfluidic chip to the sample bottle. Load 100 µL of biotinylated anti-EpCAM (10 µg/mL in PBS with 1% (w/v) BSA and 0.09% (w/v) sodium azide) into the sample bottle. Fill full of the microfluidic chip with the solution. Incubate for 30 min Wash with PBS.

2. Pressure 1 mL of patient blood sample through the microfluidic chip at the flow rate (1 mL/h).
3. Gently wash microfluidic chip with 100 µL PBS.
4. Fill full of the microfluidic chip with 4% paraformaldehyde (PFA) in PBS for fixing cells captured on substrate for 20 min.
5. To stain and visualize captured cells, replace the PFA with 0.2% Triton X-100 in PBS and incubate for 10 min
6. Next, fill the microfluidic chip with 100 µL of fluorophore-labeled antibody solution (20 µL/1 mL initial concentration) and incubate the microfluidic chip in the dark at 4° C. overnight. Wash the microfluidic chip with 200 µL PBS at flow rate 1 mL/h
7. Fill 100 µL DAPI solution (1×DAPI reagent in 1 mL of DI water) into microfluidic chip and incubate for 5 min Wash the microfluidic chip with 200 µL PBS.
8. Unclap the microfluidic layer from substrate and invert substrate onto a standard cover glass.
1. Select fluorescent microscope settings.
   1.1. Optimized exposure times
      1.1.1. DAPI (blue) filter: 50 ms exposure time (background: ~1300)
      1.1.2. FITC (green) filter: 300 ms exposure time (background: ~1600)
      1.1.3. TRITC (red) filter: 100 ms exposure time (background: ~1300)
   1.2 Digitizer should be set to 1 MHz. Other settings will yield very high background in green filter.
2. Place sample on microscope and focus on edge of substrate. Once focused, switch filter to DAPI
   2.1. Starting in the upper right corner of the substrate, scan for nuclei that are approx. 7 to 20 µm in diameter at 4× or 10× magnification.
   2.2. Increase magnification to 10× or 20× when a putative cell has been located. Using a microscope mouse, check fluorescence intensity under DAPI, TRITC, and FITC fluorescence. Sample fluorescence intensity >2× background fluorescence intensity is scored as a positive result.
3. Cells that demonstrate dual staining (red: anti-cytokeratin PE+ and blue: DAPI+) and meet standard phenotypic and morphological characteristics should be scored as CTCs. Cells that show dual staining (green: anti-CD45 FITC+ and blue: DAPI+) should be excluded as lymphocytes/non-specific cells. Items that demonstrate staining in all three filters (green+ and red+ and blue+) should be excluded as cell debris.

All publications cited herein are hereby incorporated by reference in their entirety.

REFERENCES CITED HEREIN ARE LISTED BELOW FOR CONVENIENCE (1) Steeg, P. S. Tumor metastasis: mechanistic insights and clinical challenges. *Nat Med* 12, 895-904 (2006).
(2) Budd, G. T. et al. Circulating Tumor Cells versus Imaging—Predicting Overall Survival in Metastatic Breast Cancer. *Clinical Cancer Research* 12, 6403-6409 (2006).
(3) Allard, W. J. et al. Tumor Cells Circulate in the Peripheral Blood of All Major Carcinomas but not in Healthy Subjects or Patients With Nonmalignant Diseases. *Clinical Cancer Research* 10, 6897-6904 (2004).
(4) Zieglschmid, V., Hollmann, C. Böocher, O. DETECTION OF DISSEMINATED TUMOR CELLS IN PERIPHERAL BLOOD. *Critical Reviews in Clinical Laboratory Sciences* 42, 155-196 (2005).
(5) Cristofanilli, M. et al. Circulating Tumor Cells, Disease Progression, and Survival in Metastatic Breast Cancer. *The New England Journal of Medicine* 351, 781-791 (2004).
(6) Racila, E. et al. Detection and characterization of carcinoma cells in the blood. *Proceedings of the National Academy of Sciences of the United States of America* 95, 4589-4594 (1998).
(7) Krivacic, R. T. et al. A rare-cell detector for cancer. *Proceedings of the National Academy of Sciences of the United States of America* 101, 10501-10504 (2004).
(8) Nagrath, S. et al. Isolation of rare circulating tumour cells in cancer patients by microchip technology. *Nature* 450, 1235-1239 (2007).
(9) Adams, A. et al. Highly Efficient Circulating Tumor Cell Isolation from Whole Blood and Label-Free Enumeration Using Polymer-Based Microfluidics with an Integrated Conductivity Sensor. *J Am Chem Soc* 130, 8633-8641 (2008).
(10) Smirnov, D. A. et al. Global Gene Expression Profiling of Circulating Tumor Cells. *Cancer Research* 65, 4993-4997 (2005).
(11) Huang, L. R., Cox, E. C., Austin, R. H. & Sturm, J. C. Continuous Particle Separation Through Deterministic Lateral Displacement. *Science* 304, 987-990 (2004).
(12) Chang, W. C., Lee, L. P. & Liepmann, D. Biomimetic technique for adhesion-based collection and separation of cells in a microfluidic channel. *Lab Chip* 5, 64-73 (2005).
(13) Toner, M. & Irimia, D. BLOOD-ON-A-CHIP. *Annual Review of Biomedical Engineering* 7, 77-103 (2005).
(14) Domagala, W. & Koss, L. Configuration of surfaces of human cancer cells in effusions. *Virchows Archiv B Cell Pathology Zell-pathologie* 26, 27-42 (1978).

We claim:

1. A method of selectively isolating biological cells from a cell sample comprising:
   contacting the cell sample to a device for capturing biological cells under conditions that permit binding agents of the device to selectively bind a subpopulation of biological cells, resulting in bound biological cells; and
   removing unbound biological cells from the device,
   wherein the device comprises:
      a substrate comprising a nanostructured surface region;
      a plurality of binding agents attached to the nanostructured surface region of the substrate; and
      a flow layer attached to said substrate to form a microfluidic channel such that at least a portion of said nanostructured surface region of said substrate is in contact with fluid that flows through said microfluidic channel while in operation,
      wherein the nanostructured surface region comprises a plurality of nanostructures each having a longitudinal dimension and lateral dimension, the longitudinal dimension being at least ten times greater than the lateral dimension,
      wherein biological cells are selectively captured by the binding agents and the plurality of nanostructures acting in cooperation,
      wherein said flow layer comprises a textured surface that causes chaotic flow to increase the probability that said biological cells come into contact with said nanostructured surface region of said substrate to be captured.

2. A method according to claim 1, further comprising washing the captured biological cells with an aqueous medium.

3. A method according to claim 1, wherein the cell sample comprises one or more of body fluid, plasma, saliva, spinal fluid, and urine.

4. A method according to claim 1, wherein the subpopulation of biological cells comprises circulating tumor cells.

5. A method of selectively isolating at least one target biological cell from a cell sample comprising:
  providing a cell sample containing at least one target biological cell;
  providing a device comprising:
    a substrate comprising a nanostructured surface region;
    a plurality of binding agents attached to the nanostructured surface region of the substrate; and
    a flow layer attached to said substrate to form a microfluidic channel such that at least a portion of said nanostructured surface region of said substrate is in contact with fluid that flows through said microfluidic channel while in operation,
  wherein the nanostructured surface region comprises a plurality of nanostructures each having a longitudinal dimension and lateral dimension, the longitudinal dimension being at least ten times greater than the lateral dimension,
  wherein biological cells are selectively captured by the binding agents and the plurality of nanostructures acting in cooperation,
  wherein said flow layer comprises a textured surface that causes chaotic flow to increase the probability that said biological cells come into contact with said nanostructured surface region of said substrate to be captured;
  contacting the cell sample to a plurality of nanostructures to result in the target biological cell(s) being captured, under conditions effective for the target biological cell(s) to bind to the binding agents attached to the nanostructures, resulting in bound biological cell(s).

6. A method according to claim 5, further comprising washing the bound biological cell(s) with an aqueous medium.

7. A method according to claim 5, further comprising detecting the presence of the target biological cell(s).

8. A method according to claim 5, wherein the cell sample comprises one or more of body fluid, plasma, saliva, spinal fluid, and urine.

9. A method according to claim 5, wherein the target biological cell(s) comprises a circulating tumor cell(s).

10. A method according to claim 5, wherein the plurality of binding agents comprises one or more of DNA, peptides, aptamers, and antibodies.

11. A method according to claim 5, wherein said plurality of binding agents comprises a plurality of over-expressed antibodies for tumor cells.

12. A method according to claim 5, wherein said plurality of binding agents is a plurality of anti-epithelial-cell adhesion molecule antibodies (anti-EpCAM).

13. A method according to claim 5, wherein said plurality of binding agents is a plurality of antibodies for immune cells.

* * * * *